(12) United States Patent
Eder et al.

(10) Patent No.: US 6,393,924 B1
(45) Date of Patent: May 28, 2002

(54) TESTING METHOD FOR NON-DESTRUCTIVE TESTING OF A WELDED CONNECTOR, A TESTING DEVICE AND AN ULTRASONIC WELDING APPARATUS HAVING SUCH A DEVICE

(75) Inventors: Erich Eder, Velden; Josef Reithmaier, Gerzen, both of (DE)

(73) Assignee: Schunk Ultraschalltechnik GmbH, Wettenberg (DE)

( * ) Notice: Subject to any disclaimer, the term of this patent is extended or adjusted under 35 U.S.C. 154(b) by 0 days.

(21) Appl. No.: 09/554,069

(22) PCT Filed: Nov. 10, 1997

(86) PCT No.: PCT/EP98/07166
§ 371 (c)(1),
(2), (4) Date: Jul. 19, 2000

(87) PCT Pub. No.: WO99/24810
PCT Pub. Date: May 20, 1999

(30) Foreign Application Priority Data

Nov. 10, 1997 (DE) .......................................... 197 49 682

(51) Int. Cl.[7] .............................................. G01N 3/20
(52) U.S. Cl. .................................................... 73/850
(58) Field of Search .......................... 73/849, 850, 851; 324/227, 232

(56) References Cited

U.S. PATENT DOCUMENTS

| 3,678,738 A | | 7/1972 | Jubelt |
| 3,916,304 A | * | 10/1975 | Roemer et al. ................ 324/64 |
| 4,503,392 A | * | 3/1985 | Farstritsky et al. ......... 324/232 |
| 4,826,067 A | | 5/1989 | Butler |
| 5,028,381 A | * | 7/1991 | Dugue ........................ 376/252 |
| 5,412,997 A | | 5/1995 | Dyi-chung et al. |

FOREIGN PATENT DOCUMENTS

| DE | 19 51 288.0 | 12/1970 |
| DE | 21 04 545 | 10/1971 |
| DE | 87 16 705.0 | 4/1988 |
| DE | 43 47 796 A1 | 5/1995 |
| DE | 44 47 073 | 7/1996 |
| JP | 09021736 A | 1/1997 |
| JP | 09079960 A | 3/1997 |

\* cited by examiner

*Primary Examiner*—Max Noori
(74) *Attorney, Agent, or Firm*—Sughrue Mion, PLLC

(57) ABSTRACT

In testing a method for non-destructive testing of a welded assembly which includes a plurality of strands of electrical conductors which are joined together into a bundle by ultrasonic welding, a defined testing force is introduced into two or more shell surface segments of the welded assembly in directions oriented substantially towards each other or substantially to a comon intersection. For carrying out the testing method, a testing device and a welding machine which constitute such a testing device are provided.

24 Claims, 4 Drawing Sheets

TESTING METHOD FOR NON-DESTRUCTIVE TESTING OF A WELDED CONNECTOR, A TESTING DEVICE AND AN ULTRASONIC WELDING APPARATUS HAVING SUCH A DEVICE

FIELD OF THE INVENTION

The invention relates to a non-destructive method of testing a weld comprising a plurality of strands of electrical conductors joined together into a bundle by ultrasonic welding. Furthermore the invention relates to a testing apparatus for implementing the cited test method and to an ultrasonic welding machine having such an apparatus.

"Weld" in this context covers any welded connection comprising, more particularly, the following properties. Firstly, two or more stripped strands are joined together by an ultrasonic welding method. It is understood that a strand of an electrical conductor or cable comprises a plurality of single wires. The single wires are designed to conduct an electrical current and are normally made of copper or some other material as generally appreciated in the field concerned. Ultrasonic welding is characterized by each of the single wires to be joined together being heated up by vibration, disrupting the surfaces of the single wires, smoothing out surface irregularities and thus achieving a weld. The stripped strands are typically arranged parallel to each other and then welded to each other cylindrically by some kind of section over a predetermined length. More particularly, jointing is also promoted by the single wires being crimped together.

PRIOR ART

Welds of the aforementioned kind need to be fabricated very often in producing wiring harnesses. These can be wiring harnesses for motor vehicles, commercial vehicles as well as for components for aircraft and marine applications. In producing a wiring harness on a so-called makeup board a weld is produced directly in the wiring harness by an ultrasonic welder in creating an electrical connection between several electrical conductors.

If inspection were to find a weld to be insufficient or unsatisfactory, i.e. failing to produce a satisfactory electrical connection or lacking in mechanical (bonding) strength when the wiring harness has already been installed, the entire damaged wiring harness would need removing as a whole and to be replaced new. This is prohibitively costly and time-consuming. Accordingly, it is especially in just-in-time production in automotive engineering not permitting any delay, that it is unacceptable for wiring harnesses to be installed with faulty or NO GO (defective) welds.

This is why attempts have been made to develop test methods which permit testing the welds (welded connections) produced prior to the wiring harnesses being installed. However, to date only tests could be implemented which involve destroying the weld. For this purpose peel or bending tests have been developed, pull tests implemented and micrographs analyzed. For one thing, this is unacceptable economically since this also involves destroying GO welds at great expense. For another, this test method can be carried out naturally only on a sampling basis, thus risking NO GO wiring harnesses being installed.

It is due to this that attempts have already been made to check the welding properties already in the ultrasonic welding machine. For this purpose an internal quality control, a so-called inspector was installed in the system for monitoring a plurality of trouble sources such as for example oxydized conductors, grease or oil inclusions in the weld, copper quality. In addition the weld is gauged to establish its degree of density from the ratio of height to width. However, this test method is also complicated and inaccurate.

Attempts have also been made to obtain an indication as to the quality of the weld already during welding by testing its ring in sound. This involves simulating various factors having a negative influence on the weld. But this method too, failed to lead to any positive result. Also investigated was the possibility of a ultrasound or eddy current test since these methods are already put to use in checking for inclusions in castings or for welding seam quality assessment. However, this composition bears no comparison with those in a weld of the aforementioned kind since unlike welded strands a solid structure is involved, thus making it relatively easy to analyze the quality.

SUMMARY OF THE INVENTION

The technical problem on which the invention is based involves comprising a method of non-destructively testing a weld of the aforementioned kind which is simple and reliable in application, also in accompanying the process to permit obtaining a certain indication as to the strength and electrical conductivity of the weld.

This technical problem is solved by a test method having the features of claim 1. The non-destructive test method in accordance with the invention is characterized in that a defined testing force is introduced into two or more shell surface segments of the weld in directions oriented substantially towards each other or substantially to a common intersection.

The gist of the invention is based on applying a pressure to the structure of a weld of the aforementioned kind such that should a NO GO weld be involved a discernible change occurs, whereas a GO weld results in no such change and thus there is no destruction of the weld. For the first time it is now possible in accordance with the invention to make use of the "uncoiling" of the wires making up the strands of electrical conductors welded to each other only superficially occurring only with slight pressure loading when the weld is a NO GO.

From exhaustive tests it has been discovered that the difference between the defined testing force and the force at which a fault already occurs when the weld is a NO GO is relatively large. Thus, the force needed to test a GO weld is roughly 2.5 to 1.25 times the force needing to be applied to produce a discernible change for a NO GO weld. For example, a force of 1,000 N turned out to be sufficient as the testing force for non-destructively testing a weld made up of copper single wires having a width of 2.8 mm and a height of 2.1 mm with a ram to anvil length of 6.5 mm.

The testing force to be applied depends, of course, on the cross-sections, size and material of the single wires making up the strands of the electrical conductors as well as on the welded conditions set on the ultrasonic welding machine. However, in accordance with the invention a method of non-destructively testing such a weld is now made available for the first time which is defined by a pressure test. For this purpose it is, of course, necessary that the testing force is applied as best possible without notching the weld and that, in addition, sufficient clearance remains at the periphery of the weld so that a NO GO weld produces an uncoiling effect and thus a "bloating" of the single wires for observation. This means that the nesting jaws suitable, for example, for applying the testing force in a testing apparatus do not cover the full shell circumference. Due to this it is a great advantage when the defined testing force is applied as an elongated load substantially along shell lines or narrow shell surface segments of the weld.

Due to the fact that the testing force is increased continuously from a low starting value to a defined testing force, especially in a linear increase, any commencement of a NO GO or uncoiling of the single wires in the weld is very quickly discernible. More particularly, when the force profile is plotted and analyzed any NO GO can be very quickly sensed and alerted as desired, for example, by a visual or audible indication.

As already explained, the defined testing force depends on the type of weld involved and on the conditions in ultrasonic welding. However, in general it can be said that the defined testing force is 2.5 to 1,25 times higher than the force resulting in a first discernible change in a NO GO weld.

Welds of the aforementioned kind are generally configured square or round in cross-section. Where such welds are concerned, applying the force is preferably done to two opposing longitudinal edge portions. Where oval or elliptical cross-sections are involved the force is correspondingly applied to opposing main or ancillary apexes. In the same way, where symmetrical cross-sections are involved the force is applied to advantage to opposing shell surface segments in the region of the longitudinal centerline. Otherwise, of course, applying the force to two or more longitudinal edge portions or general shell surface segments is possible and expedient.

An apparatus for implementing the aforementioned test method comprises the features as set forth in claim 11. This apparatus is characterized by two or more nesting jaws movable in directions oriented substantially towards each other or on a common intersecting direction, each of which is formed so that a weld to be tested is nested along a shell surface segment. In addition a means is needed for squeezing the nesting jaws together with a defined testing force which is so high that no disruption results with a GO weld whereas a discernible change occurs in a NO GO weld.

For this purpose the nesting jaws may be configured greatly differingly to comply with the cross-sections of the weld to be tested. For example, a wedge shape is suitable with or without a parallel arrangement of scores, notches or the like on the faces contacting the weld. However, concave or convex nesting jaws, especially of round or oval cross-sections, are also expedient.

In one preferred embodiment of the testing apparatus a means of limiting the testing force is provided to restrict the testing force capable of being applied as a maximum. The testing force is adaptable correspondingly to the nature of the weld to be tested.

In principle any NO GO condition of the weld may be discerned visually since an "uncoiling" occurs in such a NO GO condition, resulting in the outer shape of the test object changing. To advantage, however, a means of sensing the change, for example in the form of a strain gauge, force sensor or the like is provided with which the change occurring in the case of a NO GO weld can be sensed. This may also be, for example, a displacement sensor. It is on the basis of of an alert signal output by the sensing means that a visual and audible alert indication is given.

Applying the force is done preferably pneumatically or hydraulically assisted, but may of course also be applied manually in the case of small cross-sections or small testing forces.

By incorporating such a testing apparatus in or directly at the output of an ultrasonic welding machine for welding a plurality of strands of electrical conductors each made up of single wires into a weld of polygonal, round or oval cross-section, 100% testing can now be implemented facilitated and cost-effectively.

BRIEF DESCRIPTION OF THE DRAWINGS

Several embodiments of the invention will now be detailed for a better understanding with reference to the attached drawings in which.

DETAILED DESCRIPTION OF EXAMPLE EMBODIMENTS OF THE INVENTION

Figure 1:
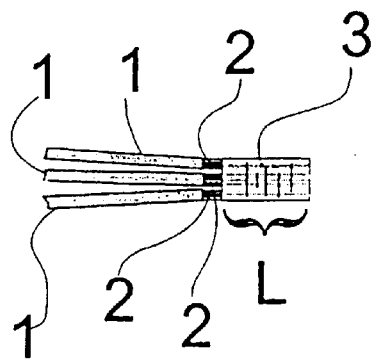
FIG. 1 is a schematic side view of a weld to be tested comprising a plurality of strands of electrical conductors joined together into a bundle by ultrasonic welding.
Figure 2:
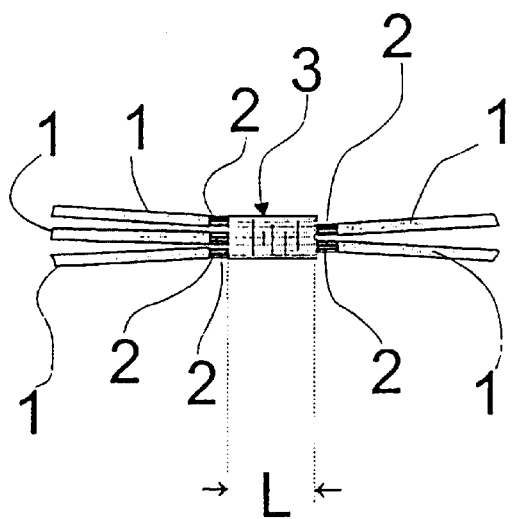
FIG. 2 is a schematic side view of a further configuration of a weld to be tested.
Figure 4:
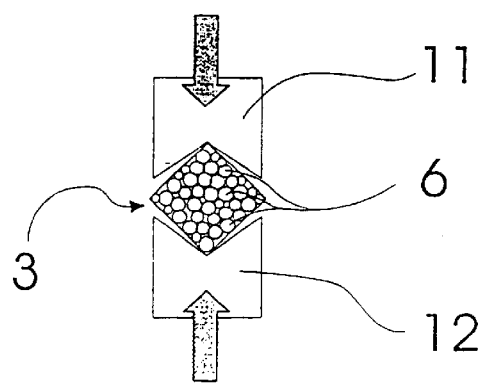
FIG. 4 is a schematic illustration of the testing procedure for a square weld.
Figure 12:
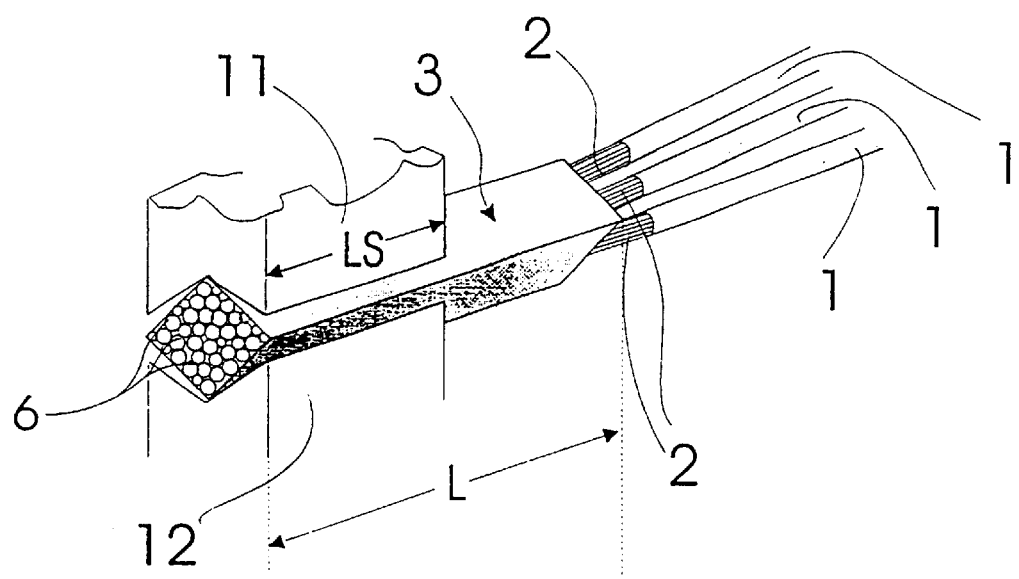
FIG. 12 is a view in perspective view of an end weld to be tested which, for a better Appreciation, is shown inserted in only one nesting jaw.

The basic configuration of a weld 3 to be tested by a test method in accordance with the invention for a GO weld is evident more particularly from the FIGS. 1, 2 and 12. In principle, a weld 3 to be tested comprises a plurality of stripped strands 2 of electrical conductors 1. Each strand 2 of an electrical conductor 1 is made up of a plurality of single wires 6 as evident, for example, from the cross-section show in FIG. 4. Over the length L the individual strands 2 of the electrical conductors 1 or, more particularly, the single wires 6 of the plurality of strands 2 have been joined together with an ultrasonic welding juxtaposed in parallel. This means that the individual strands 2 or single wires 6 "bond" to each other at the surface due to a combination of vibration frequency and mechanical pressure. This results in a good electrical contact. It is usual that rectangular or square cross-sections are formed in ultrasonic welding. However, of course, also round, oval, elliptical or also generally polygonal cross-sections can be produced.

Referring now to FIG. 1 there is illustrated a weld as a so-called end weld 3. An end weld 3 is characterized in that all stripped strands 2 of the electrical conductors 1 are located parallel to each other on the same side of the weld 3. In contrast to this, in FIG. 2 there is illustrated a weld 3 in which the stripped strands 2 of various conductors 1 run together from two face sides. But, these strands 2 too, are arranged parallel to each other.

Figure 3:
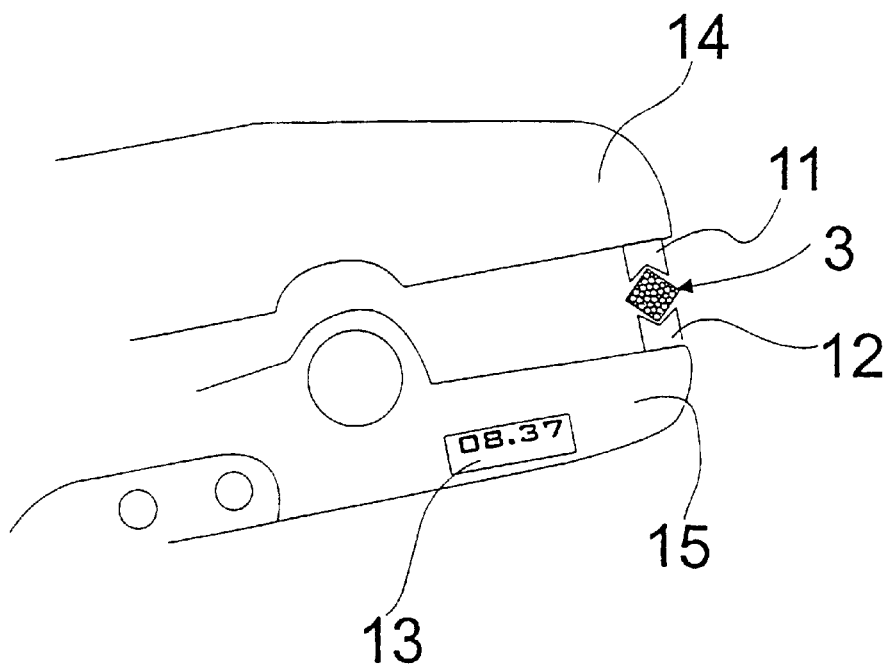
FIG. 3 is a schematic illustration of a testing apparatus in accordance with the invention, in this case test pliers, for non-destructively testing a weld of square cross-section.

Irrespective of the cross-section of the weld 3 both the electrical connection of the weld and the mechanical strength need to be assured. Referring now to FIG. 3 there is illustrated test pliers in accordance with the invention as may be used for this purpose, for example. The test pliers comprises an upper nesting jaw part 14 and a lower nesting jaw part 15. Integrated in the lower nesting jaw part is a display 13 indicating the testing force. The upper nesting jaw part 14 and the lower nesting jaw part 15 are rotatively joined together via a hinge joint. Each upper nesting jaw part and lower nesting jaw part comprises nesting jaws 11, 12 respectively.

In the example embodiment of the test pliers as shown in FIG. 3 the nesting jaws 11, 12 are configured wedge-shaped. The shape of the wedge is selected so that the angle included therein is greater than the corner angle of the weld 3. For testing, the weld 3 is inserted in the nesting jaws 11, 12 so that it applies the testing force to the diagonal longitudinal edges of the weld 3. For this purpose the nesting jaws 11, 12 are moved towards each other. This is illustrated schematically in FIG. 4. A GO weld 3 produces no discernible, in this case visually discernible, change when subjected to the testing force.

Figure 5:
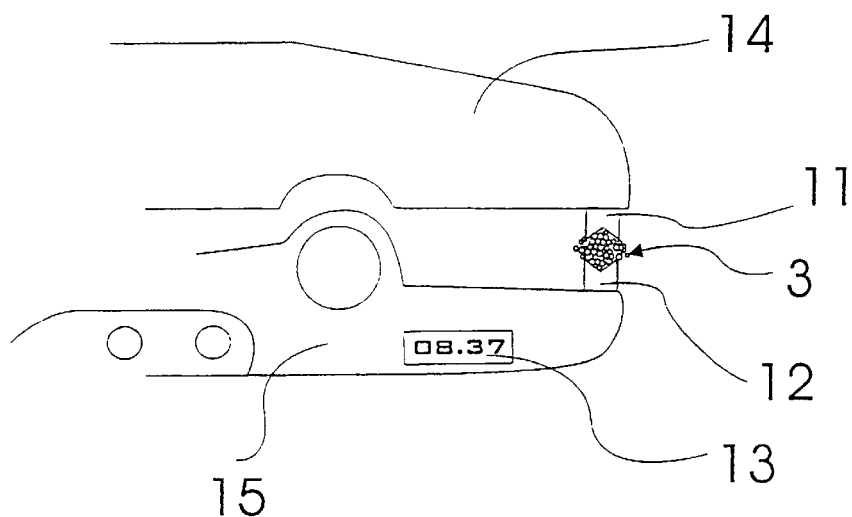
FIG. 5 is a schematic side view of a testing apparatus in accordance with the invention including a NO GO weld.
Figure 6:
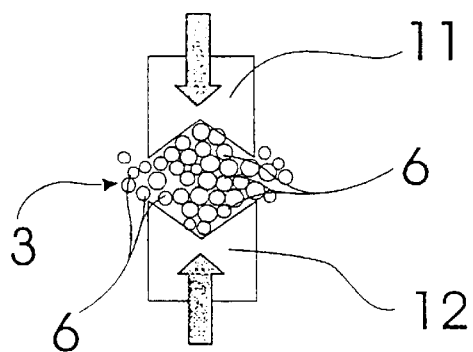
FIG. 6 is a magnified view of the NO GO weld as shown in FIG. 5.

Referring now to FIG. 5 there is illustrated by contrast how the same testing force produces a change in the weld 3 visually discernible, for instance. The weld 3 is disrupted by the testing force applied via the nesting jaws 11, 12. An "uncoiling" of the single wires 6 of the single strands 2 connected on the surface to each other. This means the surface connection of the single wires 6 of the strand 2 rupture; in the single wires 6 "uncoil" from each other. A magnified illustration of this "uncoiling" action is better evident from FIG. 6.

Figure 7:
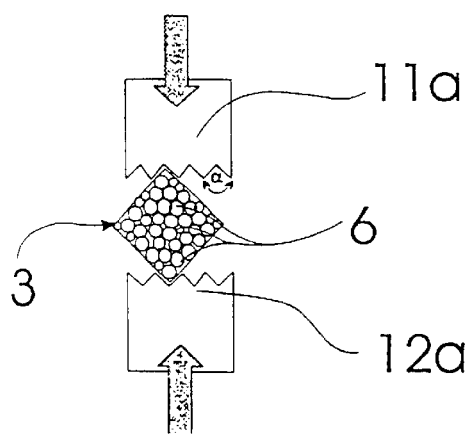
FIG. 7 is a schematic view illustrating another configuration of the nesting jaws.

Referring now to FIG. 7 there is illustrated a further aspect in the shape of the nesting jaws 11a and 12a. These nesting jaws 11a, 12a comprise several wedge-shaped grooves oriented parallel to each other. Each groove has an inner angle α which is larger than the outer angle of the longitudinal edge portions of the weld 3 to be gripped by the nesting jaws 11a, 12a. This results in the testing force being introduced merely via the opposing longitudinal edge portions into the weld 3 to be tested.

Figure 8:
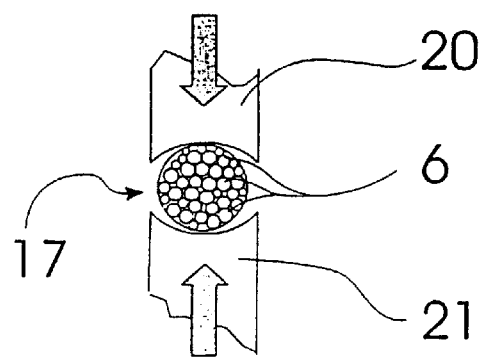
FIG. 8 is a schematic illustration of how the nesting jaws are configured for a round cross-section weld.

Referring now to FIG. 8 there is illustrated schematically the aspect of nesting jaws 20, 21 for a weld 17 having a round cross-section. The round cross-section weld 17 is made up of single wires 6 joined together by the ultrasonic welding method. To apply the testing force to the two opposing narrow shell surface segments of the weld 17 each of the nesting jaws 20, 21 is configured concave. In this arrangement the radii of the nesting jaws 20, 21 are selected larger than the radius of the cross-section of the weld 17 to be nested in the jaws.

Figure 9:
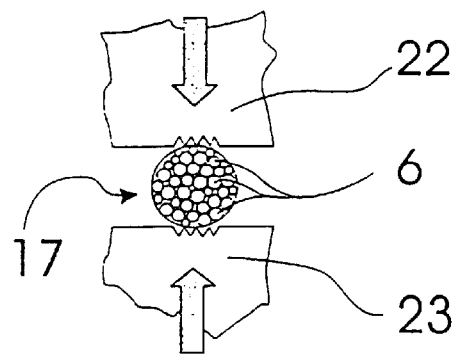
FIG. 9 is a further illustration of how the nesting jaws are configured for a round cross-section weld.

Referring now to FIG. 9 there is illustrated how the nesting jaws can be configured correspondingly differingly, however, for testing a weld 17 of round cross-section. In this case the nesting jaws 22, 23 as shown are flat and comprise microserrations to prevent the weld 17 to be tested from slipping out of place. These microserrations in the form of grooves, notches or scorings in the nesting jaws 22, 23 must not, of course, cause any notching in the weld 17 to be tested.

Figure 10:
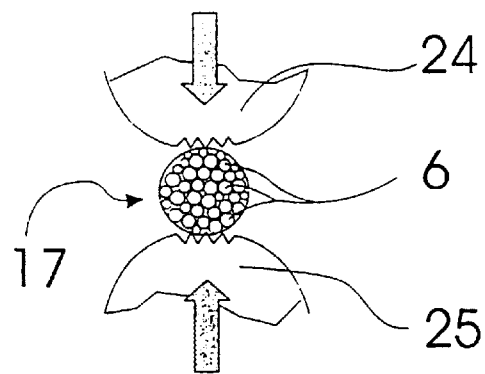
FIG. 10 is yet a further illustration of how the nesting jaws are configured for a round cross-section weld.

Referring now to FIG. 10 there is illustrated yet a further aspect of the jaws for a weld 17 having a round cross-section or of some other shape. In this case the nesting jaws 24, 25 are configured convex to nest the weld 17 to be tested at two opposing narrow shell surface segments. Advantageously, the two nesting jaws 24, 25 comprise a microserration or the like to prevent the weld 17 to be tested from slipping out of place. The radii of the nesting jaws 24, 25 in this case can be selected relatively freely, but it is good practice to select them at least as large or larger than the radius of the weld 17 to be tested.

Figure 11:
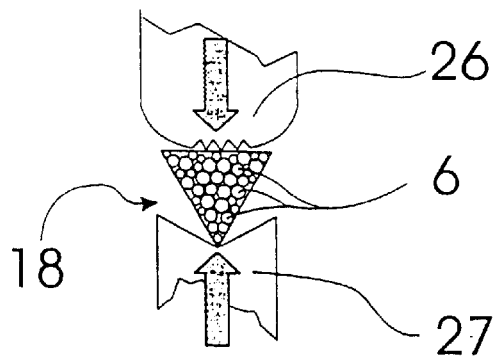
FIG. 11 is a schematic illustration of the test procedure for a weld of triangular cross-section and showing the nesting jaws provided herefor as an example.

Referring now to FIG. 11 there is illustrated in conclusion the shape of the jaws for a weld 18 having a triangular cross-section. In the embodiment as shown in this case one nesting jaw 26 is configured convex. The other nesting jaw 27 comprises, as already explained, a wedge shape. The weld 18 to be tested is nested in this case by one longitudinal edge at the wedge-shaped nesting jaw 27. The opposing flat side of the weld 18 is held by the convex nesting jaw 26.

Referring now to FIG. 12 there is illustrated in perspective how the weld 3 to be tested is to be nested in the jaws. The weld shown in this case is made up of three merging, stripped strands 2 of electrical conductors 1. In the ultrasonic welding method the single wires 6 of the strands 2 are crimp-welded in a square cross-section over a length L. The weld in this case is thus an end weld. The weld 3 is then placed in the two opposing wedge-shaped nesting jaws 11 (only one of which is shown). Each nesting jaw has a length LS which in this case is smaller than the length of the weld 3. However, the length LS may also be the same as the length L of the weld. The weld 3 of square cross-section is nested by the wedge-shaped nesting jaws 11 at two opposing longitudinal edge portions, to which a testing force is applied. Optimally in this case the testing force is introduced only into the very narrow longitudinal edge portion of the weld diagonally.

An end weld 3 tested as an example was approx. 15 mm long. It had a height of 2.1 mm and a width of 2.8 mm. The ram and anvils of the ultrasonic welding machine were 6.5 mm long. The testing force for testing the weld 3 comprising the dimensions and features as described above to be applied via the wedge-shaped nesting jaws 11, 12 was 1,000 N. No change was observed in the weld 3 on applying the testing force of 1,000 N. Thus the weld could be assessed as sufficient and satisfactory. Any incorrect welding of the weld would have produced a discernible change or damage in the weld at a testing force of already 600–700 N, i.e. by the "uncoiling" effect occurring.

As already indicated in the background description it is of course just as possible to already apply the testing force by means of two or more nesting jaws directly after welding in the ultrasonic welding machine.

What is claimed is:

1. A method of non-destructively testing a welded assembly, the welded assembly comprising a plurality of strands of electrical conductors which are joined together into a bundle by ultrasonic welding, the method including the step of introducing a defined testing force into at least two shell surface segments of said welded assembly, the testing force being introduced into the at least two shell surface segments in directions which are oriented substantially towards each other or in directions which are substantially oriented towards a common intersection.

2. The method as set forth in claim 1, wherein said defined testing force is applied as a uniform load substantially along shell lines or narrow shell surface segments of said welded assembly.

3. The method as set forth in claim 1, wherein said testing force is increased continuously from a low starting value to a defined testing force.

4. The method as set forth in claim 3, wherein said increase is linear.

5. The method as set forth in claim 1, wherein said testing force is 2.5 to 1.25 times higher than the force which, in case of a defective welded assembly, results in a discernible alteration of the welded assembly.

6. The method as set forth in claim 1, wherein said welded assembly has a polygonal cross-section and said defined testing force is introduced at least at two opposing longitudinal edges of the cross-section.

7. The method as set forth in claim 6, wherein said defined testing force is applied at diagonally opposed longitudinal edges of the cross-section.

8. The method as set forth in claim 1, wherein said welded assembly has an odd-number polygonal cross-section and said defined testing force is introduced along at least one longitudinal edge of the cross-section and a shell surface portion opposing this longitudinal edge.

9. The method as set forth in claim 1, wherein said welded assembly has an elliptical cross-section and said defined testing force is introduced at shell surface segments opposing each other in the region of the main or ancillary apex of the cross-section.

10. The method as set forth in claim 1, wherein said welded assembly has a symmetrical cross-section and said defined testing force is introduced at shell surface segments opposing each other in the region of the axis of symmetry of the cross-section.

11. The method as set forth in claim 1, wherein said defined testing force is introduced over a partial length of said welded assembly amounting to at least 20% of the total length of said welded assembly.

12. A testing apparatus for non-destructive testing a welded assembly, the welded assembly comprising a plurality of strands of electrical conductors which are joined together into a bundle by ultrasonic welding, said apparatus comprising:

two or more nesting jaws movable in directions which are oriented substantially towards each other or towards a common intersection, each of the jaws being formed so that a welded assembly to be tested is nested along a shell surface segment, and a means for squeezing said nesting jaws together with a defined testing force which is so high that no damage results with a faultless welded assembly, whereas a discernible alteration occurs in a defective welded assembly.

13. The testing apparatus as set forth in claim 12, wherein at least one of said nesting jaws having the shape of a wedge at said side for nesting said welded assembly, the interior angle of said wedge being greater than the outer angle of said longitudinal edge portion of said welded assembly which is to be nested by said nesting jaw.

14. The testing apparatus as set forth in claim 12, wherein the inner surface areas of at least one nesting jaw, which surface faces the wedged assembly to be nested, comprises several grooves oriented parallel to each other.

15. The testing apparatus as set forth in claim 12, wherein the inner surface area of at least one nesting jaw, which surface faces the wedged assembly to be nested, is configured concave.

16. The testing apparatus as set forth in claim 12, wherein the inner surface area of at least one nesting jaw, which surface faces the wedges assembly to be nested, is configures convex.

17. The testing apparatus as set forth in claim 12, wherein the inner surface areas of at least one nesting jay, which surface faces the wedges assembly to be nested, is configured substantially flat, said surface being machined serrated with grooves, depressions or ridges.

18. The testing apparatus as set forth in claim 12, wherein a means of limiting sadi testing force is provided which restricts said testing force to be applied as a maximum.

19. The testing apparatus as set forth in claim 12, wherein a sensing means is provided for sensing said alteration occurring in case of a defective welded assembly.

20. The testing apparatus as set forth in claim 19, wherein said sensing means is a displacement sensor.

21. The testing apparatus as set forth in claim 19, wherein said sensing means is a force sensor.

22. The testing apparatus as set forth in claim 19, wherein an indicator is provided which outputs an audible or visual alert on the basis of an error signal output by said sensing means.

23. The testing apparatus as set forth in claim 12, wherein it is configured as a pliers for manual or pneumatic or hydraulic actuation.

24. An ultrasonic welding machine for welding a plurality of strands of electrical conductors each made up of single wires into a bundle of polygonal, round or oval cross-section, comprising a test apparatus as set forth in claim 12.

* * * * *